United States Patent
Berens et al.

(10) Patent No.: US 8,841,474 B2
(45) Date of Patent: Sep. 23, 2014

(54) PROCESS FOR PREPARING 6-CHLORODIBENZO[D,F][1,3,2]DIOXAPHOSPHEPIN

(71) Applicant: BASF SE, Ludwigshafen (DE)

(72) Inventors: Ulrich Berens, Binzen (DE); Holger Ganz, Ludwigshafen (DE); Franz Niklaus Windlin, Heidelberg (DE); Alexander Tishkov, Moskau (RU)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/731,847

(22) Filed: Dec. 31, 2012

(65) Prior Publication Data
US 2013/0172596 A1    Jul. 4, 2013

Related U.S. Application Data

(60) Provisional application No. 61/581,650, filed on Dec. 30, 2011.

(51) Int. Cl.
*C07F 9/6571* (2006.01)
*C07F 9/6574* (2006.01)

(52) U.S. Cl.
CPC ........... *C07F 9/6571* (2013.01); *C07F 9/65744* (2013.01); *C07F 9/65746* (2013.01)
USPC .......................................................... 558/84

(58) Field of Classification Search
None
See application file for complete search history.

(56) References Cited

U.S. PATENT DOCUMENTS

| | | | |
|---|---|---|---|
| 4,668,651 A | 5/1987 | Billig et al. |
| 4,748,261 A | 5/1988 | Billig et al. |
| 4,769,498 A | 9/1988 | Billig et al. |
| 4,885,401 A | 12/1989 | Billig et al. |
| 5,235,113 A | 8/1993 | Sato et al. |
| 5,391,801 A | 2/1995 | Sato et al. |
| 5,663,403 A | 9/1997 | Sato et al. |
| 5,728,861 A | 3/1998 | Sato et al. |
| 6,172,267 B1 | 1/2001 | Urata et al. |
| 2007/0112219 A1 | 5/2007 | Ortmann et al. |

FOREIGN PATENT DOCUMENTS

| | | |
|---|---|---|
| DE | 10360771 A1 | 7/2005 |
| EP | 0214622 A2 | 3/1987 |
| EP | 0285136 A2 | 10/1988 |

OTHER PUBLICATIONS

International Search Report for PCT/EP2012/077022, mailing date Mar. 14, 2013.

Tsarev, V.N. et al.: "Complexing and catalytic properties of easily available chiral imino phosphite based on biphenyl-2,2'-diol", Russian Chemical Bulletin (translation of Izvestlya Akademil Nauk, Serlya Khimicheskaya), 53(4), 814-818 Coden: Robuey; ISSN: 1066-5285, 2004, XP002691293.

Anschutz, L. et al.: "Catalytic influence of phosphorus trichloride on the conversion of bivalent phenols", Naturwissenschaften, 42, 644 Coden: Natway; ISSN 0028-1042, 1955, XP002691294.

*Primary Examiner* — Sun Jae Yoo
(74) *Attorney, Agent, or Firm* — Drinker Biddle & Reath LLP

(57) ABSTRACT

The present invention relates to a process for preparing 6-chlorodibenzo[d,f][1,3,2]dioxaphospepin (I)

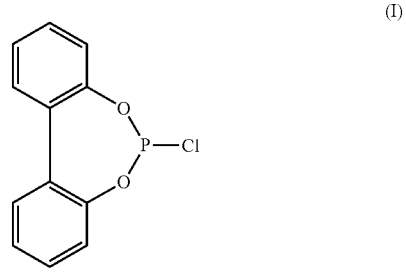

which comprises reacting 2,2'-dihydroxybiphenyl with $PCl_3$ in the presence of a catalytic amount of an acid salt of a nitrogen base, wherein the reaction is carried out in the absence of external organic solvents.

19 Claims, No Drawings

PROCESS FOR PREPARING 6-CHLORODIBENZO[D,F][1,3,2] DIOXAPHOSPHEPIN

RELATED APPLICATIONS

This application claims benefit (under 35 USC 119(e)) of U.S. Provisional Application Ser. No. 61/581,650, filed Dec. 30, 2011, which is incorporated herein by reference in its entirety.

BACKGROUND OF THE INVENTION

The present invention relates to a process for preparing 6-chlorodibenzo[d,f][1,3,2]dioxaphosphepin (2,2'-biphenylphosphomonochloridite).

PRIOR ART

Organic diphosphite compounds have found extremely widespread use, for example as chelating ligands in homogeneous catalysis and also as flame retardants, UV stabilizers, etc. Particular rhodium complexes comprising chelating diphosphite compounds have been found to be useful as catalysts for the hydroformylation of olefins, since they firstly have a high catalytic activity and secondly lead to predominantly linear aldehydes which are preferred for many applications. Organic diphosphite compounds are also suitable as ligands for transition metal complex catalysts for hydrocyanation, hydrogenation, carbonylation, hydroacylation, hydroamidation, hydroesterification, hydrosilylation, hydroboration, alcoholysis, isomerization, allylic alkylation or hydroalkylation.

Such diphosphite compounds, their preparation and their use as ligands in a hydroformylation process are described, for example, in EP 0 214 622 A2, EP 0 285 136 A2, U.S. Pat. Nos. 4,668,651, 4,748,261, 4,769,498, 4,885,401, 5,235,113, 5,391,801, 5,663,403, 5,728,861, 6,172,267 and DE 103 60 771 A1.

Organic diphosphites of the general formula (4) are usually prepared by a process which comprises the following steps:

a) reaction of a compound of the formula (1) (=first aromatic diol) with phosphorus trichloride to give the phosphochloridite (2)

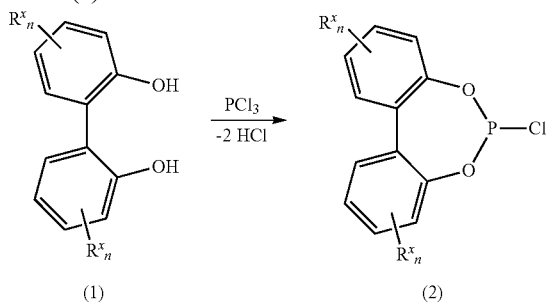

b) reaction of the phosphochloridite (2) with a compound of the formula (3) (=second aromatic diol) to give the chelating diphosphite (4)

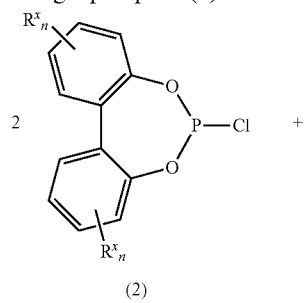

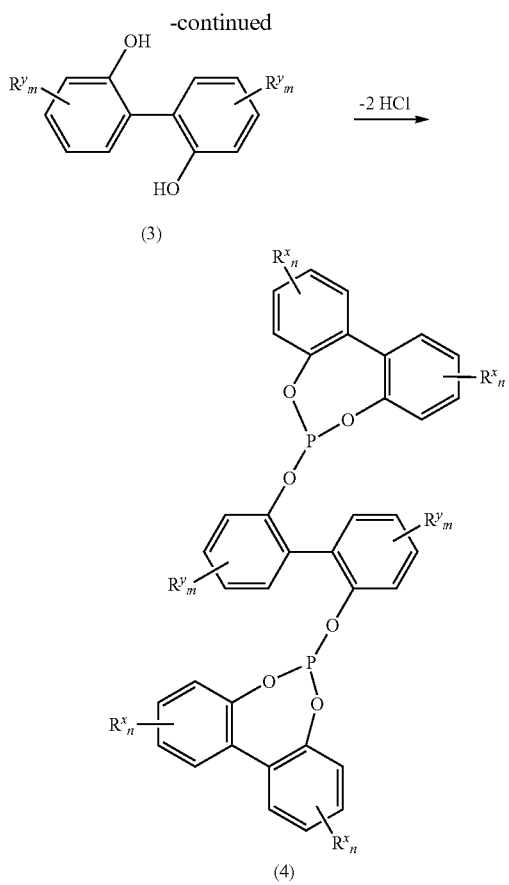

The groups of the organic diphosphites which are derived from the first aromatic diol (1) will hereinafter also be referred to as "side wings".

Phosphochloridites of the formula (2) and especially 6-chlorodibenzo[d,f][1,3,2]dioxaphosphepin are thus important intermediates in the preparation of ligands for many homogeneous transition metal catalysts. There is therefore a continual need for processes which allow preparation of these compounds with very effective utilization of the starting materials in very high yields and good purity. Owing to the toxicity and corrosivity of PCl$_3$, there is a need for processes which make possible a very low excess of the PCl$_3$ used in the synthesis in order to keep the streams to be handled in the synthesis, recycling and disposal as small as possible.

In the preparation of phosphomonochloridites and chelating diphosphites, hydrogen halide is obtained in the condensation reaction of the alcohols or phenols used with PCl$_3$ and this has to be removed from the reaction mixture. One possibility is neutralization with a base, with nitrogen bases frequently being used. In this procedure, an at least stoichiometric amount of base based on the hydrogen halide liberated has to be used. The base is frequently also used in excess. Catalytic activity of the hydrohalic acid salts of the nitrogen bases in the condensation reactions has not hitherto been described.

WO 2003/062171 and WO 2003/062251 describe a process for the removal of acids from reaction mixtures by means of an auxiliary base which with the acid forms a salt which is liquid at temperatures at which the desired product is not significantly decomposed during the removal of the liquid salt and the salt of the auxiliary base with the desired product or the solution of the desired product in a suitable solvent forms two immiscible liquid phases. In other words, the acid salts of the auxiliary base behave like ionic liquids which are essentially immiscible with the actual reaction solvent. Preferred auxiliary bases of this type are 1-methylimidazole, 1-n-butylimidazole, 2-methylpyridine and 2-ethylpyridine. The processes described in WO 2003/062171 and WO 2003/062251 are suitable, inter alia, for phosphorylation reactions such as the above-described synthesis of phosphomonochloridites and the reaction thereof with an aromatic diol to give a chelating diphosphite compound. According to the teaching of WO 2003/062171 and WO 2003/062251, the nitrogen base is used in an at least stoichiometric amount based on hydrogen halide liberated.

CN 101684130A describes a process for preparing chelating phosphites, in which the phosphomonochloridite forming the side wings is introduced as a solution in dichloromethane into the reaction and the aromatic diol which bridges the two phosphorus atoms is introduced as a solution in triethylamine or a triethylamine/dichloromethane mixture. To prepare the phosphochloridite, the document teaches reacting the aromatic diol with from 1 to 10 equivalents of $PCl_3$ and distilling off excess $PCl_3$. The use of an acid salt of a nitrogen base as catalyst is not described. In the specific examples, 2,2'-biphenol is reacted with $PCl_3$ at 100° C. in the absence of organic solvent. The reaction thus occurs below the melting point of 2,2'-biphenol, i.e. as a suspension of the diol in a large excess of $PCl_3$ (molar ratio of diol:$PCl_3$=1:6.1). In addition, this document indicates that when the unpurified phosphochloridite obtained in this way is used in a solvent other than dichloromethane, e.g. toluene, only turbid suspensions are obtained because of the impurities present. However, the inventors of the present invention were able to demonstrate the contrary for the inventive process described below.

WO 2010/052090 and WO 2010/052091 describe processes for preparing 6-chlorodibenzo[d,f][1,3,2]-dioxaphosphepin, in which 2,2'-dihydroxybiphenyl is added as a melt or as a suspension in an inert solvent to an excess of phosphorus trichloride under inert gas while stirring and the gases formed are discharged from the reaction mixture and neutralized. This process has the disadvantage that the $PCl_3$ has to be used in a large molar excess over the diol. Thus, according to the general teaching of these documents, a from 2- to 25-fold excess is used, while an approximately 12-fold excess is used in the examples. These documents do not teach carrying out the reaction in the presence of a catalyst.

WO 2008/124468 describes a calixarene-bisphosphite composition for use as ligand in a transition metal complex catalyst. In example 1(a), the preparation of 2,2'-biphenylphosphomonochloridite is described. Here, 3.7 equivalents of $PCl_3$ are added at room temperature to one equivalent of o,o'-biphenyldiol and the suspension obtained is subsequently heated until the evolution of HCl abates and subsequently distilled in a high vacuum, with the desired phosphochloridite being obtained in a 78% yield. A significant disadvantage of this procedure is that the reaction is virtually uncontrollable after mixing the reactants and is thus problematical from a safety point of view. It is less the thermal safety which is a problem, since this reaction is endothermic, but rather the risk that on the production scale the HCl discharging system can fail, for example due to an excessively high reaction rate or blockage, which can lead to a pressure buildup with the associated consequences. Furthermore, a greater capital investment is necessary since the HCl scrubber has to be made larger in order to cope with sudden larger amounts of HCl per unit time.

WO 2010/042313 describes, inter alia, a process for preparing phosphomonochloridites by reacting $PCl_3$ with an aromatic diol in a slurry which additionally comprises an organic solvent and less than 5 mol %, based on the aromatic diol, of a nitrogen base. Specifically, in example 1 of this document 2,2'-dihydroxybiphenyl is reacted as a suspension in toluene with $PCl_3$ in the presence of a catalytic amount of pyridine at 0° C. It is a critical feature of this process that a substantial part of the aromatic diol used is insoluble in the organic solvent. Thus, a large molar excess of $PCl_3$ over the diol is always available for the actual reaction in the organic phase, even though the overall molar excess of $PCl_3$ is lower. However, this document also indicates that undesirable by-products are formed at an excess of $PCl_3$ which is too low.

WO 2009/120210 and the US patent US 2009/0247790 having the same priority have a disclosure content comparable to that of WO 2010/042313. They describe a process for preparing phosphomonochloridites, in which the reaction of $PCl_3$ with an aromatic diol is carried out in a solution comprising less than 5 mol % of a nitrogen base, based on mol of aromatic diol, with HCl formed being driven off from the reaction solution and the reaction being carried out under essential isothermal conditions. For the reaction, $PCl_3$ is initially charged in a reaction zone and a solution or suspension of the diol in an organic solvent is fed into the reaction zone.

It is an object of the present invention to provide a simple, effective and safe process for preparing phosphochlorides. It should make the preparation of the phosphochloridites with very effective utilization of the starting materials in very high yields and good purity possible. The phosphochloridite compound obtained should preferably have a purity which allows it to be used as intermediate for the preparation of chelating phosphites without complicated intermediate purification.

It has now surprisingly been found that this object is achieved by a process for preparing phosphochlorides, which comprises reacting an aromatic diol with $PCl_3$ in the presence of a catalytic amount of an acid salt of a nitrogen base and in the absence of external organic solvents. It is also surprising that only very small excesses of $PCl_3$ are necessary when the $PCl_3$ is added to a melt of 2,2'-dihydroxybiphenyl, i.e. under process conditions under which the 2,2'-dihydroxybiphenyl is always present in a relatively high excess over $PCl_3$ until shortly before the end of the reaction. Furthermore, it is surprising that when the $PCl_3$ is introduced into the gas space above the surface of the melt of 2,2'-dihydroxybiphenyl, virtually no loss of $PCl_3$ due to vaporization and entrainment in the offgas stream occurs despite the significantly lower boiling point of $PCl_3$ compared to the melting point of 2,2'-dihydroxybiphenyl.

SUMMARY OF THE INVENTION

The invention provides a process for preparing 6-chlorodibenzo-[d,f][1,3,2]dioxaphosphepin (I)

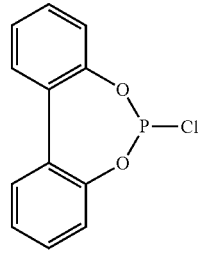

(I)

which comprises reacting 2,2'-dihydroxybiphenyl (A1)

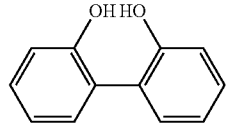

(A1)

with $PCl_3$ in the presence of a catalytic amount of an acid salt of a nitrogen base, wherein the reaction is carried out in the absence of external organic solvents.

DESCRIPTION OF THE INVENTION

For the purposes of the invention, the expression "external organic solvent" refers to components which act as solvent and are different from the starting materials and catalysts used for preparing the phosphochloridites of the general formula (I) and the reaction products formed.

The product of the 6-chlorodibenzo[d,f][1,3,2]dioxaphosphepin synthesis is soluble in toluene to give a clear solution (at 40° C. as 90% solution and at 20° C. as 50% solution) and can be used without a complicated work-up to prepare organic diphosphites. To avoid misunderstandings, it should be pointed out that the production of a toluene solution of (I) serves merely to provide (I) for subsequent reactions and does not represent a work-up or purification step.

The process of the invention has the following advantages:

It allows the preparation of 6-chlorodibenzo[d,f][1,3,2]dioxaphosphepin (I) in high yields and with good selectivities.

The chlorodibenzo[d,f][1,3,2]dioxaphosphepin is obtained in high purity.

Compared to the processes known from the prior art, the process requires a very small excess of PCl$_3$ for the synthesis of the phosphochloridite. Owing to the toxicity and the corrosivity of PCl$_3$, this is particularly advantageous since the PC$_{1-3}$ streams to be handled in the synthesis, recycling and disposal can be kept small.

Since no volatile organic solvents are used, the problem of combustion of the vapors of these solvents before the HCl formed in the condensation reaction is separated off by scrubbing with a base does not arise.

The acid salts of nitrogen bases, especially N-methylimidazolium hydrochloride, which are used as catalyst are suitable for the reaction of PCl$_3$ with aromatic diols which have a certain residual water content (up to about 0.3% by weight, based on the total weight of the diol used). A lower outlay is therefore required for drying of the diol and its storage and use under anhydrous conditions.

Both the intermediate (A3) and the undesirable by-product (A4) are found only in traces of <2% in the end product in the preparation of the phosphochloridites (I) as a result of addition of the PCl$_3$ to the initially charged diol (A1).

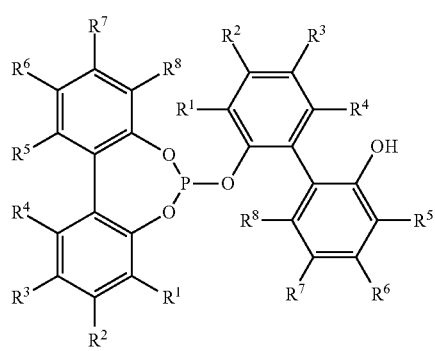

(A3)

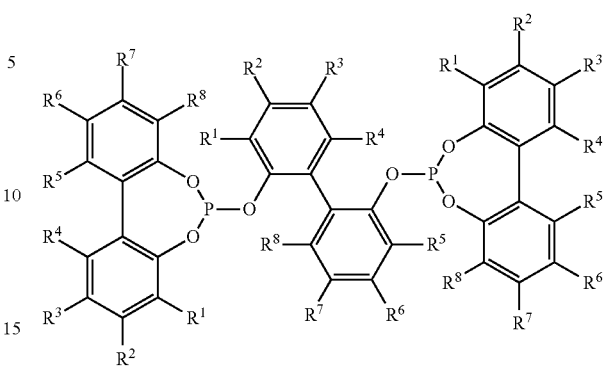

(A4)

According to the invention, the reaction of the diol (A1) with PCl$_3$ is carried out in the presence of a catalytic amount of an acid salt of a nitrogen base.

The acid salt is preferably derived from a nitrogen base selected from among in each case unsubstituted or substituted imidazoles, pyridines, 1H-pyrazoles, 1-pyrazolines, 3-pyrazolines, imidazolines, thiazoles, oxazoles, 1,2,4-triazoles and 1,2,3-triazoles.

The acid salt is particularly preferably derived from a nitrogen base selected from among in each case unsubstituted or substituted imidazoles and pyridines.

Particularly preferred nitrogen bases are 3-chloropyridine, 4-dimethylaminopyridine, 2-methylpyridine (α-picoline), 3-methylpyridine (β-picoline), 4-methylpyridine (γ-picoline), 2-ethylpyridine, 2-ethyl-6-methylpyridine, quinoline, isoquinoline, 1-methylimidazole, 1,2-dimethylimidazole, 1-(n-butyl)imidazole, 1,4,5-trimethylimidazole, 1,4-dimethylimidazole, imidazole, 2-methylimidazole, 1-butyl-2-methylimidazole, 4-methylimidazole, 1-(n-pentyl)imidazole, 1-(n-hexyl)imidazole, 1-(noctyl)imidazole, 1-(2'-aminoethyl)imidazole, 2-ethyl-4-methylimidazole, 2-ethylimidazole, 1-(2'-cyanoethyl)imidazole and benzotriazole.

In particular, the acid salt is derived from a nitrogen base selected from among 1-(C$_1$-C$_4$-alkyl)imidazoles, 2-(C$_1$-C$_4$-alkyl)pyridines, 3-(C$_1$-C$_4$-alkyl)pyridines and 4-(C$_1$-C$_4$-alkyl)pyridines.

The acid salt is especially derived from a nitrogen base selected from among 1-methylimidazole, 1-(n-butyl)imidazole, 2-methylpyridine and 2-ethylpyridine.

Acids with which the nitrogen bases can form salts are, for example, hydrogen chloride (HCl), hydrogen bromide (HBr), sulfuric acid (H$_2$SO$_4$, to form sulfates or hydrogensulfates), methylsulfuric acid (HO(SO$_2$)OCH$_3$), ethylsulfuric acid (HO(SO$_2$)OC$_2$H$_5$), phosphoric acid (H$_3$PO$_4$, to form phosphates, hydrogenphosphates or dihydrogenphosphates), p-toluenesulfonic acid, benzenesulfonic acid, benzoic acid, 2,4,6-trimethylbenzoic acid, mandelic acid, methanesulfonic acid, ethanesulfonic acid or trifluoromethanesulfonic acid. Preferred acids with which the nitrogen bases can form salts are, for example, hydrogen chloride, p-toluenesulfonic acid, methanesulfonic acid, 2,4,6-trimethylbenzoic acid and trifluoromethanesulfonic acid. Particular preference is given to hydrogen chloride.

Especially, N-methylimidazolium hydrochloride is used as acid salt of a nitrogen base in the process of the invention.

The amount of acid salt of the nitrogen base used is preferably from 0.01 to 5 mol %, particularly preferably from 0.05 to 2 mol %, in particular from 0.1 to 1 mol %, based on the molar amount of diol (A1).

In the process of the invention, the reaction of the diol (A1) with $PCl_3$ is carried out essentially without addition of free nitrogen bases. The preparation of the phosphochloridites of the general formula (I) is thus carried out according to the process of the invention not as described in WO 03/062171 and WO 03/062251. That is to say, in the process of the invention, the hydrogen chloride liberated in the reaction is not separated off by means of an auxiliary base which with hydrogen chloride forms a salt which is liquid at temperatures at which the phosphochloridites of the general formula (I) are not significantly decomposed and the phosphochloridites of the general formula (I) or a solution thereof in a suitable solvent forms two immiscible liquid phases.

The molar ratio of the gradually added $PCl_3$ to the amount of diol (A1) used is more than 1:1, preferably at least 1.1:1, in particular at least 1.2:1, at the end of the reaction.

The molar ratio of the gradually added $PCl_3$ to the amount of diol (A1) used is preferably not more than 2.5:1, particularly preferably not more than 2:1, in particular not more than 1.8:1, especially not more than 1.6:1, more especially not more than 1.4:1, at the end of the reaction.

As mentioned above, the process of the invention makes it possible to prepare 6-chlorodibenzo[d,f][1,3,2]dioxaphosphepin (I) using only a small excess of $PCl_3$.

The reaction is preferably carried out at a temperature in the range from 20 to 250° C., particularly preferably from 50 to 200° C.

In a specific embodiment of the process of the invention for preparing the phosphochloridites of the general formula (I), the diol (A1) is used as a melt for the reaction.

To provide a melt, the diol (A1) is heated to a temperature above the melting point so that it goes over into a liquid state. If the diol (A1) is used as a technical-grade compound comprising impurities which lower the melting point, the melting point can also be below that of the pure compound. Pure 2,2'-dihydroxybiphenyl melts at from 108 to 110° C.

In a specific embodiment of the process of the invention, the $PCl_3$ is added to a melt of the diol (A1).

The $PCl_3$ is preferably introduced into the space above the melt of the diol (A1). This can be achieved using a conventional addition device whose outlet opening ends above the melt. The $PCl_3$ can be introduced in the form of individual droplets or as a jet. The amount fed in can be regulated by means of a conventional metering device, e.g. a valve, metering pump, etc. The reaction can thus be carried out in a meteringcontrolled manner. At least those surfaces which come into contact with the $PCl_3$ are made of a corrosion-resistant material such as glass, Teflon, enamels, etc.

The boiling point of $PCl_3$ (76.1° C. at 1013 mbar) is below the melting point of the diol (A1) (108-110° C.). The reaction is therefore preferably carried out using one of the following measures:

addition of the $PCl_3$ in sufficiently small amounts per time interval, use of a cooling device, e.g. a reflux condenser, in order to separate off vaporized $PCl_3$ as condensate and recirculate it to the reaction zone.

In general, the reaction is carried out at ambient pressure (1013 mbar), but higher or lower pressures can also be used.

In a specific embodiment, the reaction is carried out in the presence of a gas which is inert under the reaction conditions. Suitable inert gases of this type are, for example, nitrogen, argon or helium. In a useful embodiment, the liquid reaction medium is blanketed with an inert gas. In a further useful embodiment, a stream of inert gas is passed through the liquid reaction medium. The stream of inert gas passed through the liquid reaction medium can at the same time serve to strip the reaction medium in order to remove the HCl formed more effectively. In a preferred embodiment, an offgas stream is taken from the reaction zone and subjected to scrubbing to remove the HCl comprised therein. Suitable washing media are water and aqueous alkaline washing media.

If the reaction zone is connected to a cooling device, e.g. a reflux condenser, in order to avoid $PCl_3$ losses by vaporization, the offgas stream, optionally together with at least one inert gas, is preferably also firstly passed through the cooling device and only then the offgas scrubber.

The reaction is preferably carried out until at least 95% by weight of the diol (A1), particularly preferably at least 98% by weight of the diol (A1), has been converted into 6-chlorodibenzo[d,f][1,3,2]dioxaphosphepin (I).

If the reaction mixture still comprises unreacted $PCl_3$ after the conclusion of the reaction, this can be separated off by conventional methods, preferably by distillation. To separate off the $PCl_3$ by distillation, it is possible to employ one of the following measures:

increasing the temperature of the reaction mixture, applying a reduced pressure, introducing a stream of inert gas into the reaction mixture, a combination of at least two of these measures.

The phosphochloridites obtained by the process of the invention are particularly advantageous for preparing organic diphosphites.

The invention further provides a process for preparing organic diphosphites of the general formula (II)

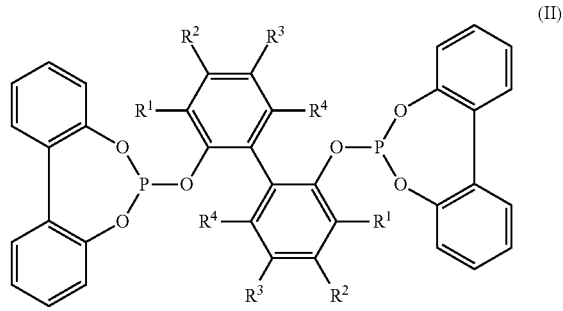

where $R^1$, $R^2$, $R^3$ and $R^4$ are each, independently of one another, hydrogen, $C_1$-$C_{12}$-alkyl, $C_1$-$C_{12}$-alkoxy, $C_3$-$C_{12}$-cycloalkyl, $C_3$-$C_{12}$-heterocycloalkyl, $C_6$-$C_{20}$-aryl, chlorine, bromine, hydroxy, acyl or alkoxycarbonyl, where two adjacent radicals $R^1$ to $R^4$ together with the carbon atom of the benzene ring to which they are bound can also form a fused ring system with a further benzene ring, where $C_1$-$C_{12}$-alkyl and $C_1$-$C_{12}$-alkoxy can each be unsubstituted or substituted by one or more identical or different radicals $R^a$ selected from among $C_3$-$C_{12}$-cycloalkyl, $C_3$-$C_{12}$-heterocycloalkyl, $C_6$-$C_{20}$-aryl, fluorine, chlorine, cyano, acyl and alkoxycarbonyl, where $C_3$-$C_{12}$-cycloalkyl and $C_3$-$C_{12}$-heterocycloalkyl can each be unsubstituted or substituted by one or more identical or different radicals Rb selected from among $C_1$-$C_{12}$-alkyl, $C_1$-$C_{12}$-alkoxy, $C_3$-$C_{12}$-cycloalkyl, $C_3$-$C_{12}$-heterocycloalkyl, $C_6$-$C_{20}$-aryl, fluorine, chlorine, bromine, cyano, formyl, acyl and alkoxycarbonyl, where $C_6$-$C_{20}$-aryl and can each be unsubstituted or substituted by one or more identical or different radicals Rc selected from among $C_1$-$C_{12}$-alkyl, $C_1$-$C_{12}$-alkoxy, $C_3$-$C_{12}$-cycloalkyl, $C_3$-$C_{12}$-heterocycloalkyl, $C_6$-$C_{20}$-aryl, fluorine, chlorine, bromine, cyano, formyl, acyl and alkoxycarbonyl, which comprises a) reacting 2,2'-dihydroxybiphenyl (A1)

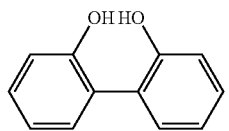
(A1)

with PCl$_3$ in the presence of a catalytic amount of an acid salt of a nitrogen base and in the absence of an external organic solvent to give 6-chlorodibenzo[d,f][1,3,2]dioxaphosphepin (I), b) reacting the 6-chlorodibenzo[d,f][1,3,2]dioxaphosphepin (I) with a diol of the general formula (A2)

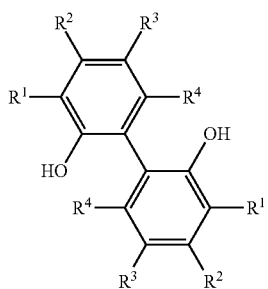
(A2)

to give the organic diphosphite (II).

For the purposes of the invention, halogen is fluorine, chlorine, bromine or iodine, preferably fluorine, chlorine or bromine.

In the following, the expression "$C_1$-$C_{12}$-alkyl" comprises straight-chain and branched $C_1$-$C_{12}$-alkyl groups. Preference is given to straight-chain or branched $C_1$-$C_8$-alkyl groups and very particularly preferably $C_1$-$C_6$-alkyl groups. Examples of $C_1$-$C_{12}$-alkyl groups are, in particular, methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

The above explanations of the expression "$C_1$-$C_{12}$-alkyl" also apply to the alkyl groups in $C_1$-$C_{12}$-alkoxy.

Substituted $C_1$-$C_{12}$-alkyl groups and substituted $C_1$-$C_{12}$-alkoxy groups can, depending on their chain length, have one or more (e.g. 1, 2, 3, 4 or 5) substituents Ra. The substituents $R^a$ are preferably selected independently from among $C_3$-$C_{12}$-cycloalkyl, $C_3$-$C_{12}$-heterocycloalkyl, $C_6$-$C_{20}$-aryl, fluorine, chlorine, bromine, cyano, formyl, acyl and alkoxycarbonyl.

For the purposes of the present invention, the expression "alkylene" refers to straight-chain or branched alkanediyl groups having preferably from 1 to 6 carbon atoms.

These include methylene (—CH$_2$—), ethylene (—CH$_2$—CH$_2$—), n-propylene (—CH$_2$—CH$_2$—CH$_2$—), isopropylene (—CH$_2$—CH(CH$_3$)—), etc.

For the purposes of the present invention, the expression "$C_3$-$C_{12}$-cycloalkyl" comprises monocyclic, bicyclic or tricyclic hydrocarbon radicals having from 3 to 12, in particular from 5 to 12, carbon atoms. These include cyclopropyl, cyclobutyl, cyclopentyl, cyclohexyl, cycloheptyl, cyclooctyl, cyclododecyl, cyclopentadecyl, norbornyl, bicyclo[2.2.2]octyl or adamantyl.

For the purposes of the present invention, the expression "$C_3$-$C_{12}$-heterocycloalkyl" comprises nonaromatic, saturated or partially unsaturated cycloaliphatic groups having from 3 to 12, in particular from 5 to 12, carbon atoms. $C_3$-$C_{12}$-Heterocycloalkyl groups preferably have from 4 to 8, particularly preferably 5 or 6, ring atoms. In contrast to the cycloalkyl groups, 1, 2, 3 or 4 of the ring carbons in the heterocycloalkyl groups are replaced by heteroatoms or heteroatom-comprising groups. The heteroatoms or heteroatom-comprising groups are preferably selected from among —O—, —S—, —C(=O)— and —S(=O)$_2$—. Examples of $C_3$-$C_{12}$-heterocycloalkyl groups are tetrahydrothiophenyl, tetrahydrofuranyl, tetrahydropyranyl and dioxanyl.

Substituted $C_3$-$C_{12}$-cycloalkyl groups and substituted $C_3$-$C_{12}$-heterocycloalkyl groups can, depending on their ring size, have one or more (e.g. 1, 2, 3, 4 or 5) substituents Rb. The substituents Rb are preferably selected independently from among $C_1$-$C_{12}$-alkyl, $C_1$-$C_{12}$-alkoxy, $C_3$-$C_{12}$-cycloalkyl, $C_3$-$C_{12}$-heterocycloalkyl, $C_6$-$C_{20}$-aryl, fluorine, chlorine, bromine, cyano, formyl, acyl and alkoxycarbonyl. Substituted $C_3$-$C_{12}$-cycloalkyl groups preferably bear one or more, e.g. 1, 2, 3, 4 or 5, $C_1$-$C_6$-alkyl groups. Substituted $C_3$-$C_{12}$-heterocycloalkyl groups preferably bear one or more, e.g. 1, 2, 3, 4 or 5, $C_1$-$C_6$-alkyl groups.

Examples of substituted $C_3$-$C_{12}$-cycloalkyl groups are 2- and 3-methylcyclopentyl, 2- and 3-ethylcyclopentyl, 2-, 3- and 4-methylcyclohexyl, 2-, 3- and 4-ethylcyclohexyl, 2-, 3- and 4-propylcyclohexyl, 2-, 3- and 4-isopropylcyclohexyl, 2-, 3- and 4-butylcyclohexyl, 2-, 3- and 4-sec-butylcyclohexyl, 2-, 3- and 4-tert-butylcyclohexyl, 2-, 3- and 4-methylcycloheptyl, 2-, 3- and 4-ethylcycloheptyl, 2-, 3- and 4-propylcycloheptyl, 2-, 3- and 4-isopropylcycloheptyl, 2-, 3- and 4-butylcycloheptyl, 2-, 3- and 4-sec-butylcycloheptyl, 2-, 3- and 4-tert-butylcycloheptyl, 2-, 3-, 4- and 5-methylcyclooctyl, 2-, 3-, 4- and 5-ethylcyclooctyl, 2-, 3-, 4- and 5-propylcyclooctyl.

For the purposes of the present invention, the expression "$C_6$-$C_{20}$-aryl" comprises monocyclic or polycyclic aromatic hydrocarbon radicals. These have from 6 to 20 ring atoms, in particular from 6 to 14 ring atoms. Aryl is preferably phenyl, naphthyl, indenyl, fluorenyl, anthracenyl, phenanthrenyl, naphthacenyl, chrysenyl, pyrenyl, coronenyl, perylenyl, etc. In particular, aryl is phenyl or naphthyl.

Substituted $C_6$-$C_{20}$-aryl groups can, depending on their ring size, have one or more (e.g. 1, 2, 3, 4 or 5) substituents $R^c$. The substituents $R^c$ are preferably selected independently from among $C_1$-$C_{12}$-alkyl, $C_1$-$C_{12}$-alkoxy, $C_3$-$C_{12}$-cycloalkyl, $C_3$-$C_{12}$-heterocycloalkyl, $C_6$-$C_{20}$-aryl, fluorine, chlorine, bromine, cyano, nitro, formyl, acyl and alkoxycarbonyl.

Substituted $C_6$-$C_{20}$-aryl is preferably substituted phenyl or substituted naphthyl. Substituted $C_6$-$C_{20}$-aryl groups preferably bear one or more, e.g. 1, 2, 3, 4 or 5, substituents selected from among $C_1$-$C_6$-alkyl groups, $C_1$-$C_6$-alkoxy groups, chlorine and bromine.

For the purposes of the present invention, the term "acyl" refers to alkanoyl or aroyl groups which generally have from 2 to 11, preferably from 2 to 8, carbon atoms. They include, for example, acetyl, propanoyl, butanoyl, pentanoyl, hexanoyl, heptanoyl-, 2-ethylhexanoyl, 2-propylheptanoyl, pivaloyl, benzoyl or naphthoyl.

For the purposes of the present invention, the term carboxylate preferably refers to a derivative of a carboxylic acid function, in particular a carboxylic ester function or a carboxamide function. Such functions include, for example, esters with $C_1$-$C_4$-alkanols such as methanol, ethanol, n-propanol, isopropanol, n-butanol, sec-butanol and tertbutanol. They also include the primary amides and their N-alkyl and N,N-dialkyl derivatives.

Fused ring systems can be aromatic, hydroaromatic and cyclic compounds joined by fusion (fused). Fused ring systems comprise two, three or more than three rings. Depending on the way in which they are joined, a distinction is made among fused ring systems between ortho-fusion, i.e. each ring shares an edge or two atoms with each adjacent ring, and peri-fusion in which a carbon atom belongs to more than two rings. Among fused ring systems, preference is given to ortho-fused ring systems.

As regards step a), what has been said above for the preparation of phosphochloridites of the general formula (I) is fully incorporated by reference.

Step b)

In the organic diphosphites of the general formula (II), preference is given to the radicals $R^3$ and $R^4$ together forming a fused-on benzene ring and $R^1$ and $R^2$ each being hydrogen, i.e. the group of the formula

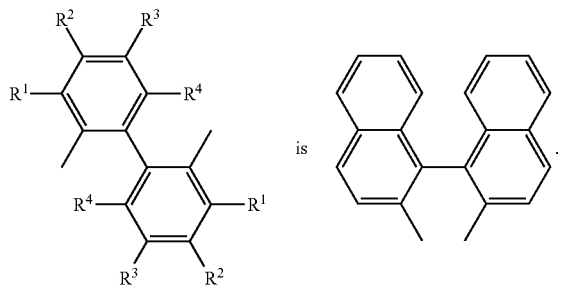

is

The diols of the general formula (A2)

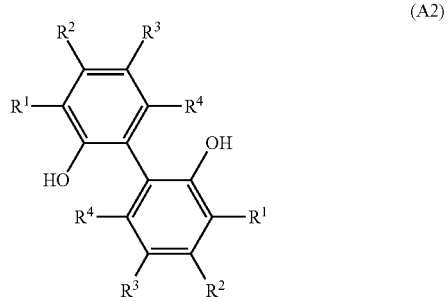

(A2)

are preferably selected from among 3,3',5,5'-tetramethyl-1,1'-biphenyl-2,2'-diol, 3,3',5,5'-tetraethyl-1,1'-biphenyl-2,2'-diol, 3,3',5,5'-tetra-n-propyl-1,1'-biphenyl-2,2'-diol, 3,3'-dimethyl-5,5'-dichloro-1,1'-biphenyl-2,2'-diol, 3,3'-diethyl-5,5'-dibromo-1,1'-biphenyl-2,2'-diol, 3,3'-dimethyl-5,5'-diethyl-1,1'-biphenyl-2,2'-diol, 3,3'-dimethyl-5,5'-din-propyl-1,1'-biphenyl-2,2'-diol, 3,3',5,5'-tetraisopropyl-1,1'-biphenyl-2,2'-diol, 3,3',5,5'-tetra-n-butyl-1,1'-biphenyl-2,2'-diol, 3,3',5,5'-tetraisobutyl-1,1'-biphenyl-2,2'-diol, 3,3',5,5'-tetra-sec-butyl-1,1'-biphenyl-2,2'-diol, 3,3',5,5'-tetra(1,1-dimethylethyl)-1,1'-biphenyl-2,2'-diol, 3,3'-di(1,1-dimethylethyl)-5,5'-di-n-amyl-1,1'-biphenyl-2,2'-diol, 3,3',5,5'-tetrakis(1,1-dimethylpropyl)-1,1'-biphenyl-2,2'-diol, 3,3'-di(1,1-dimethylethyl)-5,5'-bis(1,1-dimethylpropyl)-1,1'-biphenyl-2,2'-diol, 3,3'-di(1,1-dimethylethyl)-5,5'-di-nhexyl-1,1'-biphenyl-2,2'-diol, 3,3'-di(1,1-dimethylethyl)-5,5'-di-2-hexyl-1,1'-biphenyl-2,2'-diol, 3,3'-di(1,1-dimethylethyl)-5,5'-di-3-hexyl-1,1'-biphenyl-2,2"-diol, 3,3'-di(1,1-dimethylethyl)-5,5'-di-n-heptyl-1,1'-biphenyl-2,2"-diol, 3,3'-di(1,1-dimethylethyl)-5,5'-di-2-heptyl-1,1'-biphenyl-2,2'-diol, 3,3'-di(1,1-dimethylethyl)-5,5'-di-3-heptyl-1,1'-biphenyl-2,2'-diol, 3,3'-di(1,1-dimethylethyl)-5,5'-di-4-heptyl-1,1'-biphenyl-2,2'-diol, 3,3'-di(1,1-dimethylethyl)-5,5'-di-n-octyl-1,1'-biphenyl-2,2'-diol, 3,3'-di(1,1-dimethylethyl)-5,5'-di-2-octyl-1,1'-biphenyl-2,2'-diol, 5,5'-di-3-octyl-1,1'-biphenyl-2,2'-diol, 3,3'-di(1,1-dimethylethyl)-5,5'-di-4-octyl-1,1'-biphenyl-2,2'-diol, 3,3'-di(1,1-dimethylethyl)-5,5'-bis(1,1,3,3-tetramethylbutyl)-1,1'-biphenyl-2,2'-diol, 3,3',5,5'-tetrakis(1,1,3,3-tetramethylbutyl)-1,1'-biphenyl-2,2'-diol, 3,3'-di(1,1-dimethylethyl)-5,5',6,6'-tetramethyl-1,1'-biphenyl-2,2'-diol, 3,3'-di(1,1-dimethylethyl)-5,5'-diphenyl-1,1'-biphenyl-2,2'-diol, 3,3'-di(1,1-dimethylethyl)-5,5'-bis(2,4,6,-trimethylphenyl)-1,1'-biphenyl-2,2'-diol, 3,3'-di(1,1-dimethylethyl)-5,5'-dimethoxy-1,1'-biphenyl-2,2'-diol, 3,3'-di(1,1-dimethylethyl)-5,5'-diethoxy-1,1'-biphenyl-2,2'-diol, 3,3'-di(1,1-dimethylethyl)-5,5'-di-n-propoxy-1,1'-biphenyl-2,2'-diol, 3,3'-di(1,1-dimethylethyl)-5,5'-di-isopropoxy-1,1'-biphenyl-2,2'-diol, 3,3'-di(1,1-dimethylethyl)-5,5'-di-n-butoxy-1,1'-biphenyl-2,2'-diol, 3,3'-di(1,1-dimethylethyl)-5,5'-di-sec-butoxy-1,1'-biphenyl-2,2'-diol, 3,3'-di(1,1-dimethylethyl)-5,5'-diisobutoxy-1,1'-biphenyl-2,2'-diol, 3,3'-di(1,1-dimethylethyl)-5,5'-ditert-butoxy-1,1-biphenyl-2,2'-diol and 1,1'-binaphthalinyl-2,2'-diol.

The diol (A2) is particularly preferably 3,3',5,5'-tetra(1,1-dimethylethyl)-1,1'-biphenyl-2,2'-diol. That is to say, particular preference is given to the radicals $R^1$ and $R^3$ in the organic diphosphites of the general formula (I) all being tert-butyl and $R^2$ and $R^4$ all being hydrogen.

The 6-chlorodibenzo[d,f][1,3,2]dioxaphosphepin (I) prepared by the process of the invention is particularly useful for preparing the following organic diphosphites (II):

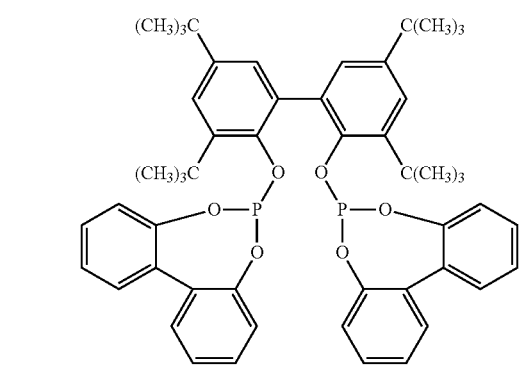

-continued

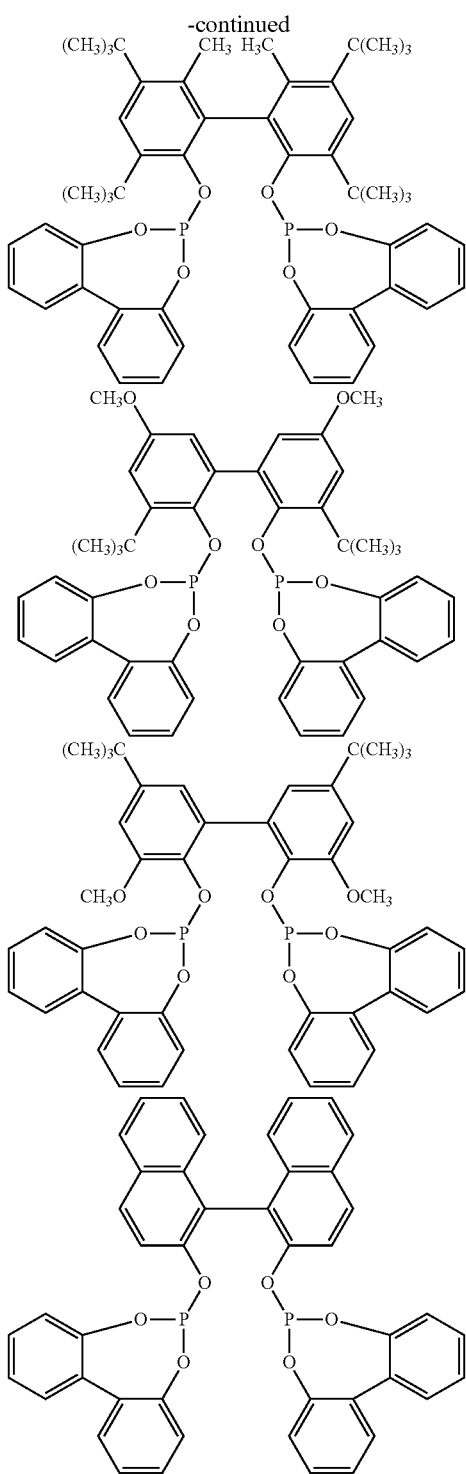

In particular, the organic diphosphite of the formula (II) is 6,6'-[[3,3',5,5'-tetrakis(1,1-dimethylethyl)-1,1'-biphenyl]-2,2'-diyl]bis(oxy)]bisdibenzo[d,f][1,3,2]-dioxaphosphepin.

Step b) of the preparation of the diphosphites (II) can in principle be carried out by means of known phosphorus halide-alcohol condensation reactions, as described, for example, in EP 0 214 622 A2, U.S. Pat. Nos. 4,668,651, 4,748,261, 4,769,498, 4,885,401, 5,235,113, 5,391,801, 5,663,403, 5,728,861, 6,172,267, WO 2003/062171 and WO 2003/062251.

The reaction in step b) is preferably carried out in the presence of a base.

Suitable bases are generally, for example, alkali metal hydroxides, alkaline earth metal hydroxides, $NO_3$, alkali metal carbonates, alkaline earth metal carbonates, alkali metal hydrogencarbonates, alkaline earth metal hydrogencarbonates, tertiary amines and basic ion-exchange resins, etc. These include, for example, NaOH, KOH, $Ca(OH)_2$, triethylamine, tripropylamine, tributylamine, etc. Preference is given to tertiary amines and more particularly triethylamine.

In a specific embodiment, the reaction in step b) is carried out by means of a process as described in WO 2003/062171 and WO 2003/062251. Here, step b) is then carried out in the presence of a base selected from among bases which with the hydrohalic acid formed in the respective reaction step form a salt which is liquid at temperatures at which the reaction product of the respective reaction step is not significantly decomposed during the removal of the liquid salt and the salt forms two immiscible liquid phases with the reaction medium of the respective reaction step.

Suitable bases of this type are described in WO 2003/062171 and WO 2003/062251, which are hereby fully incorporated by reference. Preference is given to using a base selected from among 1-methylimidazole, 1-n-butylimidazole, 2-methylpyridine and 2-ethylpyridine in step b).

In the last-named process variant, the major part of the acid salts formed from HCl and base in the condensation reaction in step b) can advantageously be removed by simple phase separation.

The organic diphosphites (II) are advantageous as ligands for catalysts for hydroformylation, hydrocyanation or hydrogenation.

The invention will be illustrated below with the aid of the following, nonlimiting example.

EXAMPLES

Example 1

Synthesis of 6-chlorodibenzo[d,f][1,3,2]dioxaphosphepin using methylimidazolium hydrochloride as catalyst 2,2'-Dihydroxybiphenyl (931.1 g, 5.0 mol) and 1-methylimidazoliumhydrochloride (0.9 g, 7.6 mmol) were placed under nitrogen in a 2000 ml double-walled reactor and, after melting of the 2,2'-dihydroxybiphenyl, heated to an internal temperature of 142° C. The introduction of $PCl_3$ (861.2 g, 6.263 mol) was then commenced with stirring, ensuring that the $PCl_3$ did not get onto the hot reactor wall. The rate of introduction was regulated so that the attached HCl scrubbing tower could completely absorb the HCl formed. A total of three hours were required for the introduction of the $PCl_3$. After the introduction of the $PCl_3$, the mixture was stirred at 140° C. for another three hours to give a fluid yellow reaction mixture. The reactor was subsequently evacuated over a period of 40 minutes to a final vacuum of 16 mbar in order to remove the excess $PCl_3$. The last residues of $PCl_3$ were removed by stirring under reduced pressure at 140° C./16 mbar and the mixture was subsequently cooled to 65° C. After admission of nitrogen, toluene (139.2 g) was added and the 90% strength solution (1390 g) of the product obtained in this way was drained into a screw-cap bottle and closed under argon. According to $^{31}$P-NMR, the product had a purity of 98.7%.

The invention claimed is:

1. A process for preparing 6-chlorodibenzo[d,f][1,3,2]dioxaphosphepin (I)

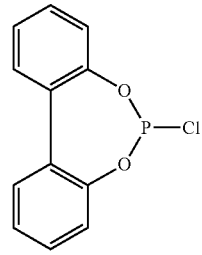

which comprises reacting 2,2'-dihydroxybiphenyl (A1)

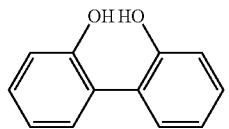

with PCl$_3$ in the presence of a catalytic amount of an acid salt of a nitrogen base, wherein the reaction is carried out in the absence of external organic solvents.

2. The process of claim 1, wherein the acid salt is derived from a nitrogen base selected from the group consisting of imidazoles, pyridines, 1H-pyrazoles, 4H-pyrazoles, 1-pyrazolines, 3-pyrazolines, imidazolines, thiazoles, oxazoles, 1,2,4-triazoles, and 1,2,3-triazoles, and wherein each member of the group is optionally unsubstituted or substituted.

3. The process of claim 1, wherein the acid salt is derived from an acid selected from the group consisting of hydrogen chloride, p-toluenesulfonic acid, methanesulfonic acid, 2,4,6-trimethylbenzoic acid, and trifluoromethanesulfonic acid.

4. The process of claim 1, wherein the acid salt of a nitrogen base is N-methyl-imidazolium hydrochloride.

5. The process of claim 1, wherein the amount of the acid salt of a nitrogen base used is from 0.01 to 5 mol %, based on the molar amount of (A1).

6. The process of claim 3, wherein the amount of the acid salt of a nitrogen base used is from 0.05 to 2 mol %, based on the molar amount of (A1).

7. The process of claim 4, wherein the amount of the acid salt of a nitrogen base used is from 0.1 to 1 mol %, based on the molar amount of (A1).

8. The process of claim 1, wherein said process is carried out essentially without addition of free nitrogen bases.

9. The process of claim 1, wherein the molar ratio of the gradually added PCl$_3$ to the amount of (A1) used is more than 1:1 at the end of the reaction.

10. The process of claim 6, wherein the molar ratio of the gradually added PCl$_3$ to the amount of (A1) used is at least 1.1:1 at the end of the reaction.

11. The process of claim 7, wherein the molar ratio of the gradually added PCl$_3$ to the amount of (A1) used is at least 1.2:1 at the end of the reaction.

12. The process of claim 1, wherein the molar ratio of the gradually added PCl$_3$ to the amount of (A1) used is not more than 2.5:1 at the end of the reaction.

13. The process of claim 1, wherein the molar ratio of the gradually added PCl$_3$ to the amount of (A1) used is not more than 2:1 at the end of the reaction.

14. The process of claim 10, wherein the molar ratio of the gradually added PCl$_3$ to the amount of (A1) used is not more than 1.8:1 at the end of the reaction.

15. The process of claim 11, wherein the molar ratio of the gradually added PCl$_3$ to the amount of (A1) used is not more than 1.6:1 at the end of the reaction.

16. The process of claim 1, wherein the molar ratio of the gradually added PCl$_3$ to the amount of (A1) used is not more than 1.4:1 at the end of the reaction.

17. The process of claim 1, wherein (A1) is used as a melt for the reaction.

18. The process of claim 1, wherein a melt of (A1) is placed in a reaction zone, and the PCl$_3$ is fed as feedstream into the reaction zone over the course of the reaction.

19. The process of claim 18, wherein the PCl$_3$ is introduced into the space above a melt of (A1).

* * * * *